United States Patent [19]

Haecker et al.

[11] 4,265,724
[45] May 5, 1981

[54] ELECTROCHEMICAL SENSOR, PARTICULARLY OXYGEN SENSOR TO DETERMINE EXHAUST GAS COMPOSITION FROM AUTOMOTIVE INTERNAL COMBUSTION ENGINES

[75] Inventors: Wolf-Dieter Haecker, Asperg; Karl-Hermann Friese, Leonberg; Bernhard Topp, Gerlingen, all of Fed. Rep. of Germany

[73] Assignee: Robert Bosch GmbH, Stuttgart, Fed. Rep. of Germany

[21] Appl. No.: 54,784

[22] Filed: Jul. 5, 1979

[30] Foreign Application Priority Data

Jul. 13, 1978 [DE] Fed. Rep. of Germany ....... 2830778

[51] Int. Cl.³ ............................................ G01N 27/58
[52] U.S. Cl. ................................................. 204/195 S
[58] Field of Search ,............................. 204/195 S, 1 S

[56] References Cited

U.S. PATENT DOCUMENTS

| | | | |
|---|---|---|---|
| 3,989,614 | 11/1976 | Tien | 204/195 S |
| 4,119,512 | 10/1978 | Inoue et al. | 204/195 S |
| 4,121,988 | 10/1978 | Sano et al. | 204/195 S |

FOREIGN PATENT DOCUMENTS 2738882  3/1978  Fed. Rep. of Germany ....... 204/195 S Primary Examiner—G. L. Kaplan
Attorney, Agent, or Firm—Frishauf, Holtz, Goodman & Woodward

[57] ABSTRACT

To improve adhesion of a porous cover layer over a platinum or platinum-rhodium electrode layer on a solid electrolyte body, for example of stabilized zirconium dioxide, the electrode layer is applied in form of interrupted, adjacent strips leaving gaps exposing the solid electrolyte body therebeneath. The porous cover layer will adhere well to the solid electrolyte body, thus protecting both the electrode and the cover layer against flaking off under high-temperature and temperature variation conditions. The sensitivity can be improved by interposing a layer of ceramic mixed with platinum or a platinum rhodium between the solid electrolyte body and at least some of the electrode strips, the adhesion of the porous cover layer over the interposed thick-film layer, where exposed between the portions of the electrode on the solid electrolyte body being sufficient for the intended purpose.

6 Claims, 4 Drawing Figures

ELECTROCHEMICAL SENSOR, PARTICULARLY OXYGEN SENSOR TO DETERMINE EXHAUST GAS COMPOSITION FROM AUTOMOTIVE INTERNAL COMBUSTION ENGINES

The present invention relates to an electrochemical sensor, and more particularly to a sensor to determine the oxygen content in the exhaust gases of internal combustion engines and especially of automotive internal combustion engines.

BACKGROUND AND PRIOR ART

Exhaust gas sensors to determine the oxygen content of exhaust gases from automotive internal combustion engines frequently use a solid electrolyte body, for example a closed tube of zirconium oxide on which an electrode system is applied, one electrode forming a measuring electrode on the electrode body which consists of a material which catalyzes the gas equilibrium at the body. To protect the material—typically a thin-film platinum electrode—a porous cover layer is applied thereover. Such sensors are introduced to the exhaust gas stream from the engine. The thin-film platinum is usually applied to the solid electrolyte, outwardly closed tube by vapor deposition. The porous cover layer is preferably a ceramic material, for example spinel. The exhaust gases from the internal combustion (IC) engine are very hot and these sensors, when exposed to the high temperatures of the exhaust gases, have a limited lifetime. It is believed that the limited life is due to damage to the thin film, for example by components in the exhaust gas itself, in that the thin film layer on the solid electrolyte loses its adhesion on the solid electrolyte body and flakes off, thus also resulting in flaking off of the protective covering layer thereover which leads to further damage to the sensor and eventually to its destruction.

THE INVENTION

It is an object to improve the sensor by improving the adhesion of layers applied at the outside of the solid electrolyte body, that is, at the side which is exposed to exhaust gases.

Briefly, the thin-film electrode is not applied on the solid electrolyte as a continuous covering, but rather in interrupted strips to leave gaps therebetween. The porous covering layer has good adhesion in the gaps on the underlying solid electrolyte body so that flaking-off of the porous layer, as well as of the electrode strip, typically thin-film platinum, is prevented.

In accordance with a feature of the invention, the solid electrolyte body can be partly covered first with layer portions forming a thick film which is made of a mixture of ceramic material and material having gas-catalyzing action, over which the electrode is then applied. Such sensors have particularly high sensitivity.

Preferably, the thin-film electrode strips are located on the side exposed to the exhaust gases in a comb-like structure, in which the solid connecting portions of the comb are located at the side of the tube which is closer to its open end, that is, away from the closed bottom, and thus away from primary exposure to the hot exhaust gases.

The sensor has the advantage that the electrode system which is formed by the thin-film electrode and the porous covering layer has sufficient adhesion to the solid electrolyte tube so that the lifetime of the sensor is substantially increased beyond that of sensors of other construction.

In a preferred form, the sensor has the shape of a tube, closed at one end, in which the closed end is introduced into the stream of the exhaust gases and exposed thereto. The comb structure, which preferably is the shape used for the electrode, is then wrapped around the tube. This construction is simple to make and does not involve any technology which cannot readily be used in connection with the previously used technology to make the sensor. It is only necessary to apply a suitable mask to the solid electrolyte body before applying the thin film electrode which is removed after the thin-film electrode is applied so that the underlying solid electrolyte body is exposed where it was masked, for subsequent covering by the porous layer.

Drawings, illustrating two preferred examples:

Figure 1:
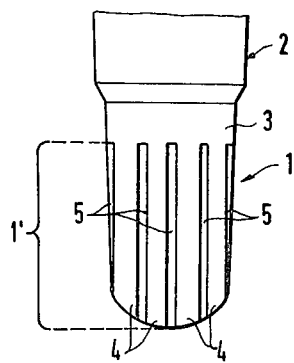
FIG. 1 is a side view of one embodiment of the sensor, in highly schematic form, and omitting those portions not necessary for an understanding of the present invention.
Figure 2:
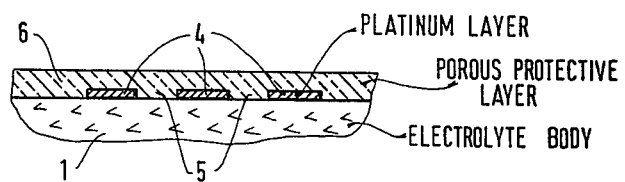
FIG. 2 is a fragmentary cross section through a sensor, in highly enlarged, and developed form.

Basic structure, embodiment of FIGS. 1 and 2: The present invention is based on the discovery that the adhesion of a porous protective layer, for example a manganese-aluminum spinel, and applied as is customary by plasma spraying, is not entirely satisfactory when applied to a thin-film electrode as such. Thus, if a thin-film electrode layer, for example platinum, is applied to a solid electrolyte body, for example of stabilized zirconium dioxide, flaking-off under severe operating conditions which are encountered in automotive applications may result.

FIG. 1 shows a solid electrolyte tube 1, closed at the bottom and formed with an open, outwardly flanged end 2. A thin-film electrode 3, preferably of platinum, is applied to the solid electrolyte tube 1 in the region of the sensing portion 1' thereof in the form of a comb which is wrapped around the tube 1, so that the lower portion thereof is formed by single tines or strips 4. The gaps 5 of ceramic surface, that is, the surface of a solid electrolyte tube 1, will remain between the strips 4. The gaps 5, which then form ceramic strips, permit good adhesion of a porous cover layer 6 (FIG. 2) which is applied over the electrode 3 and the electrode strips 4. The entire system of electrode 3, in strips 4 and the cover layer 6, provide good adhesion at the gaps or exposed portions 5 of the solid electrolyte body to provide fixation for the strips 4 as well as for the porous cover 6. The continuous portion of the thin-film electrode 3, which is close to the flanged end 2 of the body 1, ensures reliable contacting of the thin-film electrode into a housing or socket, which is not shown since it may be of any suitable and well-known construction, and reference is hereby made to the cross-referenced patents for suitable arrangements.

The structure of FIGS. 1 and 2 is preferably made this way: A sintered solid electrolyte body 1 has a mask applied thereto at the locations which will form the gaps 5, at which, at a later time, the ceramic surface of the solid electrolyte body 1 should be exposed. A protective lacquer can be applied, for example by printing or the like. The masked body 1 then has platinum vapor deposited thereon—in well known manner—and thereafter the protective lacquer mask is removed, thus leaving the structure shown in FIG. 1. The porous coating 6 is then applied by plasma-spraying, and the sensor element is finished. The electrode system comprising the thin-film electrode 3, the comb-like strips 4 and the porous cover layer 6 has excellent adhesion to the solid body 1, even under extreme operating conditions, such as high temperature, high temperature gradients, and temperature changes, vibration, and shock encountered in automotive application.

The thin-film electrode 3 preferably is platinum and is applied with a thickness of from about 0.02 to 20 μm. The porous cover layer 6 preferably is an oxide, or a mixture of several oxides, for example aluminum oxide or manganese aluminum spinel, with a thickness of from 50 to 500 μm. Other materials can be used, for example the thin-film electrode 3, 4 may be a platinum metal alloy such as a platinum-rhodium alloy. The various materials used both for the electrode as well as for the porous cover layer are well known.

Figure 3:
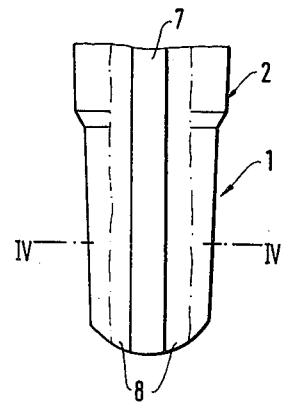
FIG. 3 is a side view of a sensor in accordance with another embodiment before application of the thin-film electrode and porous covering or coating.
Figure 4:
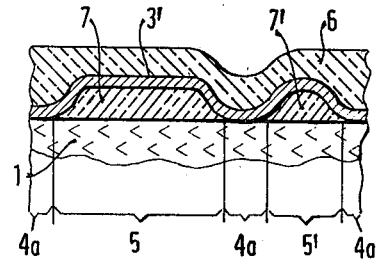
FIG. 4 is a cross section similar to FIG. 2, highly enlarged, and in developed form along line IV—IV of FIG. 3 and after the thin-film electrode—porous layer system has been applied.

It has been found that the adhesion of the electrode system which includes the thin-film electrode 3, 4 and the porous cover layer 6 on a thick-film layer 7 comprising platinum and a ceramic is sufficient for many applications. The platinum is present in a minor proportion. Sensors so constructed have a higher sensitivity. The basis for the sensor again is a tube 1, closed at the bottom, and made of stabilized zirconium dioxide, with a flanged end 2. The surface of the tube 1 has thick-film conductive strips 7 or islands 7' (FIG. 4) applied thereto. Only one strip 7 is visible in FIG. 3. The thick-film strip 7 and islands 7' consist of a mixture of platinum and a ceramic. These strips 7 and islands need not be applied accurately with sharply defined edges; rather, the edge regions 8 can be jagged, grooved, fissured and highly non-uniform. Applying a platinum-ceramic suspension by spray application will result in such strips, without clearly defined edge limits. It is particularly suitable to additionally apply small islands 7' (FIG. 4) of this thick-film platinum-ceramic material. It is even possible to entirely eliminate the strip 7 as a continuous path and apply islands 7' of the thick-film material directly on the solid electrolyte body 1. A continuous electrode system comprising layer 3' of platinum, over which the porous protective layer 6 is located, can then be applied over the body 1 with the strips 7 and islands 7' thereon, facilitating application of the electrode system and eliminating the requirement of masking. The gaps 5, and 5' (FIG. 4), of contact of the electrode 3' with body 1, that is, where the thin-film electrode 3' does not directly contact body 1 i.e. over the thick-film portions 7, 7', insure adhesion between the electrode 3' and body 1. FIG. 4 shows regions of contact of electrode 3' with the body 1 at zones 4a, and gaps 5, 5' over strips 7 and islands 7'.

The thick-film material preferably consists of platinum and ceramic in a volumetric ratio of at least 1:5, and preferably 2:5. Suitable ceramic material is, preferably, stabilized zirconium dioxide powder. Particularly high sensitivity of the sensor is obtained if the ceramic material of the solid electrolyte tube is partially stabilized zirconium dioxide with 5 mol-% $Y_2O_3$, and the ceramic material of the thick film includes entirely or fully stabilized zirconium dioxide powder with 7 mol-% $Y_2O_3$.

The thick-film ceramic has a lower sinter activity than the ceramic of the solid electrolyte body 1. Upon sintering, a particularly good porosity will result. The thick film can be applied on the already fired solid electrolyte body 1; in a particularly desirable form, however, the body 1 is only prefired and final firing is carried out together with the thick-film layers 7 and/or 7'. The metallic portion of the thick-film layer need not be platinum; platinum alloys, for example platinum-rhodium alloys, are also suitable, used, for example, together with the stabilized zirconium dioxide powder.

The solid electrolyte tube 1, with the thick-film system 7, 7' thereon, then has the electrode 3' applied by vapor deposition and the porous layer 6 is then applied thereover, to result in a structure, the cross section of which is schematically shown in FIG. 4, in which the respective thicknesses and layers, as well as gaps are greatly distorted for better illustration.

The electrode system formed by layers 3' and porous protective layer 6 adheres better on the thick-film portions 7, 7' than on the remaining portions of the body 1. The overall adhesion of the layers applied to the body 1 is substantially better than a sole electrode layer 3 and layer 6 thereover on body 1.

Various changes and modifications may be made within the scope of the inventive concept, and features described in connection with one of the embodiments may be used with the other, as well as with various types of sensors, for example of various known types, as described in the literature and in the referenced patents.

We claim:

1. Electrochemical sensor, particularly to determine oxygen content in the exhaust gases from automotive internal combustion engines comprising
   a solid electrolyte body (1) having a sensing portion (1');
   a thin-film electrode (3, 3') on said electrolyte body of a material which catalyzes the gas equilibrium of gases to which the sensor is exposed;
   and a porous cover layer (6)
   wherein, in accordance with the invention,
   the thin-film electrode (3, 4) consists of a material consisting of at least one: platinum; platinum alloy; platinum-rhodium and is located on and in direct contact with the solid electrolyte body (1) in form of partial, spacially interrupted and electrically interconnected covering portions thereon, leaving gaps (3) between the direct contact of said covering portions of thin-film electrode and on the solid electrolyte body (1); and
   the porous cover layer (6) comprises at leasat one: a ceramic oxide; a mixture of several ceramic oxides and covers the entire sensing portion including the thin-film electrode material, and the solid electrolyte body in the region of the gaps (5) between the electrodes, to provide for direct contact of the porous cover layer (6) with the solid electrolyte body (1).

2. Sensor according to claim 1, wherein the interrupted portions are strip-like.

3. Sensor according to claim 1, wherein (FIGS. 1, 2) the thin-film electrode (3, 3') comprises a comb-like structure, the interrupted portions are strip-like elements forming the tines of the comb, and a continuous connecting portion interconnecting the tines of the comb.

4. Sensor according to claim 3, wherein the solid electrolyte body is a closed tube, and the interconnecting portion is positioned near the open end of the closed tube, the tines extending essentially longitudinally along the tube towards the closed end thereof.

5. Sensor according to claim 1, wherein the solid electrolyte body (1) comprises stabilized zirconium dioxide.

6. Sensor according to claim 1, wherein the porous cover layer (6) comprises at least one of: aluminum oxide; manganese-aluminum spinel.

* * * * *